(12) United States Patent
Hillairet et al.

(10) Patent No.: US 7,932,331 B2
(45) Date of Patent: Apr. 26, 2011

(54) POLYMERISATION OF ETHYLENE AND α-OLEFINS WITH IMINO-QUINOLINOL COMPLEXES

(75) Inventors: Caroline Hillairet, Soignies (BE); Guillaume Michaud, Lille (FR); Sabine Sirol, Horrues (BE)

(73) Assignee: Total Petrochemicals Research Feluy, Seneffe (Feluy) (BE)

( * ) Notice: Subject to any disclaimer, the term of this patent is extended or adjusted under 35 U.S.C. 154(b) by 136 days.

(21) Appl. No.: 12/282,261

(22) PCT Filed: Mar. 7, 2007

(86) PCT No.: PCT/EP2007/052112
§ 371 (c)(1),
(2), (4) Date: Jan. 23, 2009

(87) PCT Pub. No.: WO2007/104680
PCT Pub. Date: Sep. 20, 2007

(65) Prior Publication Data
US 2010/0004411 A1 Jan. 7, 2010

(30) Foreign Application Priority Data
Mar. 10, 2006 (EP) .................... 06110970

(51) Int. Cl.
C08F 4/64 (2006.01)
C08F 4/69 (2006.01)
C08F 4/80 (2006.01)
C08F 4/52 (2006.01)

(52) U.S. Cl. ........ 526/161; 526/172; 526/130; 526/169; 526/169.1; 526/348; 526/351; 526/352; 556/51; 556/57; 556/138; 502/113

(58) Field of Classification Search .................. 526/172, 526/161; 556/551, 57, 138, 51
See application file for complete search history.

(56) References Cited

OTHER PUBLICATIONS

Hata et al., Bull. Chem. Soc. Jpn., 1972, 45, 477-481.*
Reihsig et al., J. Pract. Chem., 1966, 31, 167-168.*
Hata, Takehisa et al., "New Derivatives of 8-Quinolinol as Chelating Agents. I. Syntheses, Coloration Reaction with Metal Ions and Acid Dissociation Constants of Some Azomethine and Aminomethyl Derivatives," Bulletin of the Chemical Society of Japan, 45(2), 1972, pp. 477-481.
J. Reihsig, et al., "Chelate Catalysis XVII," Journal for Practical Chemistry, Series 4, vol. 31, 1966, pp. 167-178.

* cited by examiner

*Primary Examiner* — Rip A. Lee
(74) *Attorney, Agent, or Firm* — Tenley R. Krueger

(57) ABSTRACT

The present invention discloses active oligomerization or polymerization catalyst systems based on imino-quinolinol complexes.

14 Claims, 2 Drawing Sheets

POLYMERISATION OF ETHYLENE AND α-OLEFINS WITH IMINO-QUINOLINOL COMPLEXES

The present invention relates to the field of single site catalyst systems based on imino-quinolinol complexes and suitable for oligomerising or polymerising ethylene and alpha-olefins.

A multitude of catalyst systems available for polymerising or oligomerising ethylene and alpha-olefins exist, but there is a growing need for finding new systems capable to tailor polymers with very specific properties. More and more post-metallocene catalyst components based on early or late transition metals from Groups 3 to 10 of the Periodic Table have recently been investigated such as for example those disclosed in Gibson and al. review (Gibson, V. C.; Spitzmesser, S. K., in Chem. Rev. 2003, 103, p. 283). But there is still a need to improve either the specificities or the performances of these systems.

Schiff bases derivatives of 8-hydroxyquinoline-2-carboxaldehyde are known in the literature (J. Reihsig; H. W. J. Krause in J. Praktische Chemie 1966, 31, p 167; T. Hata; T. Uno in Bull. Chem. Soc. Jpn. 1972, 45, p 477), but corresponding complexes have never been described as catalysts for polymerisation of olefins.

Figure 1:
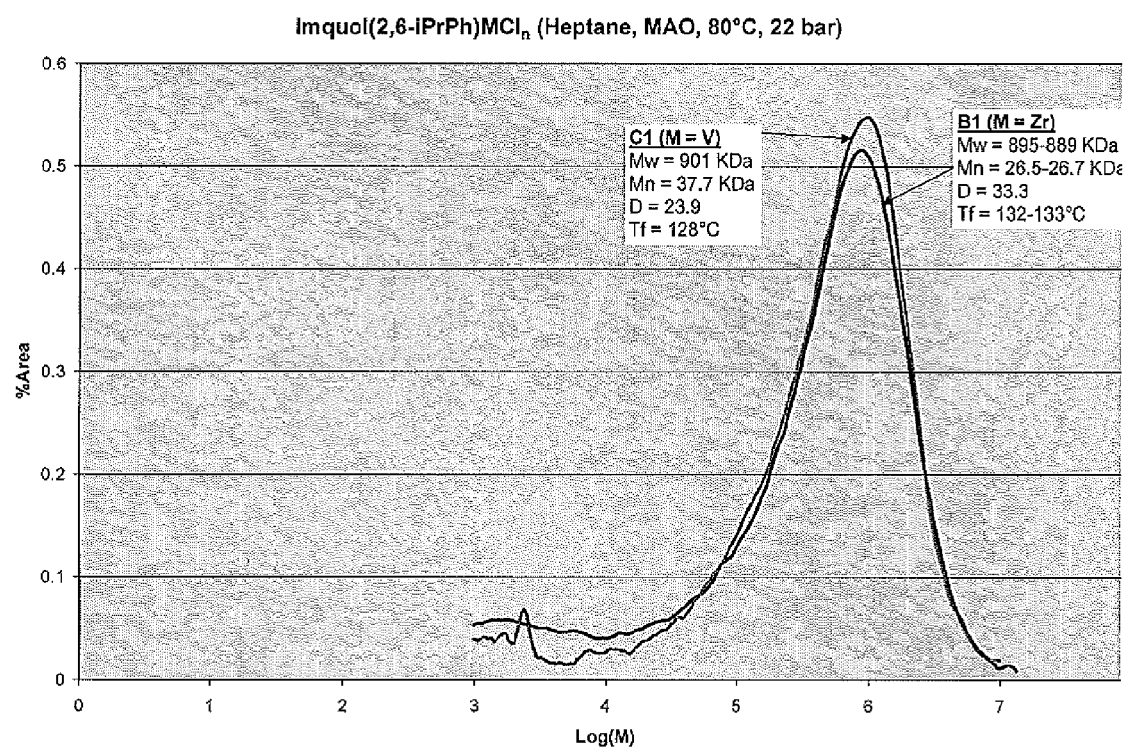
Figure 2:
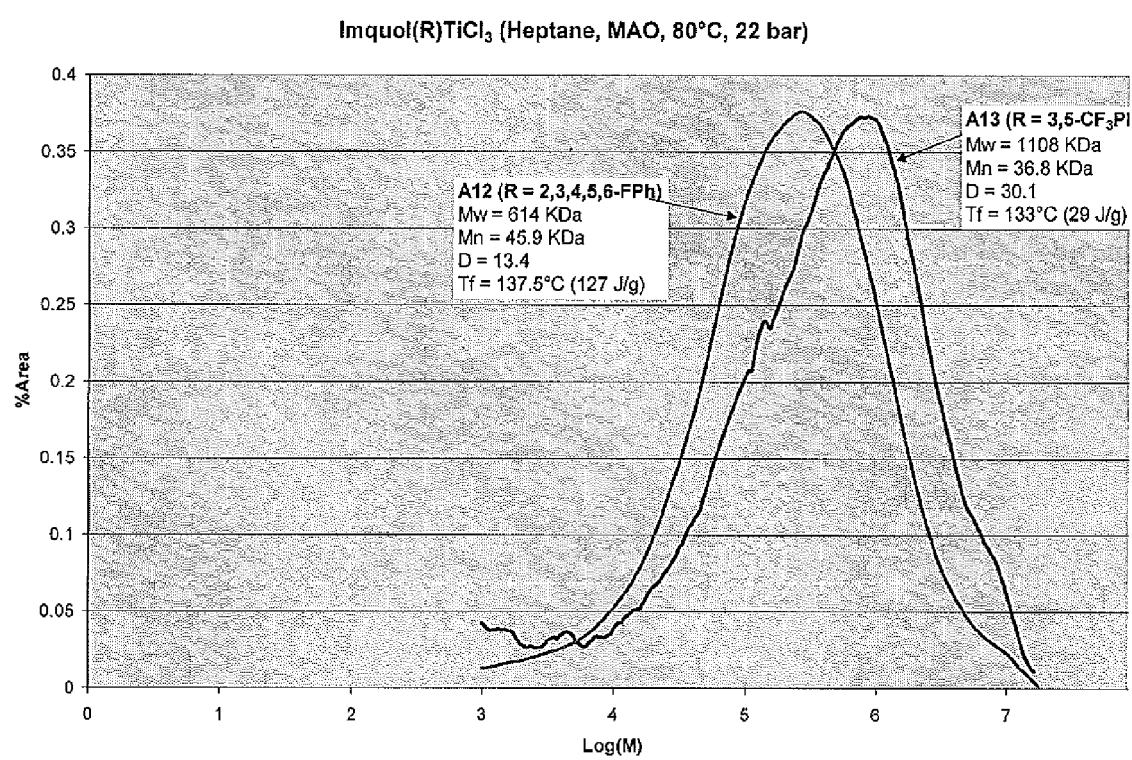

FIGS. 1 and 2 illustrate GC analysis of various ligand structures formed in the Examples.

The aim of this invention is to provide new single site catalysts based on tridentate 8-hydroxyquinoline Schiff bases ligands active in olefin polymerisation.

It is another aim of the present invention to provide active catalyst systems based on these catalyst components.

It is a further aim of the present invention to provide a process for polymerising or for oligomerising ethylene and alpha-olefins with these new catalyst systems.

Accordingly, the present invention discloses a ligand of general formula I or II

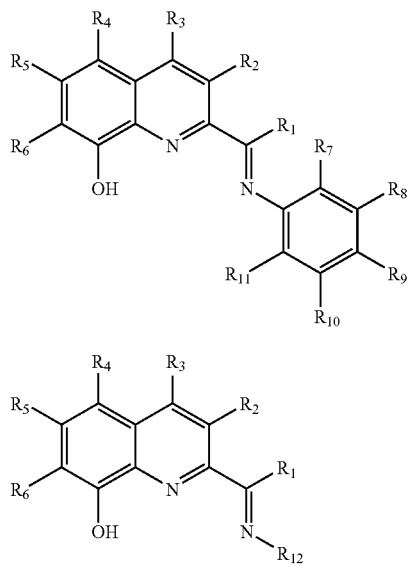

wherein $R_1$, $R_2$, $R_3$, $R_4$, $R_5$, $R_6$, $R_7$, $R_8$, $R_9$, $R_{10}$, $R_{11}$ and $R_{12}$ are each independently selected from hydrogen, halogen, unsubstituted or substituted hydrocarbyl, or inert functional group. Two or more of those groups can themselves be linked together to form further ring or rings.

Preferably $R_1$, $R_2$, $R_3$, $R_4$, $R_5$ and $R_6$, are the same and are hydrogen, $R_7$, $R_8$, $R_{10}$ and $R_{11}$ are hydrogen or alkyl or alkoxy, $R_9$ is hydrogen or alkyl having at least 2 carbon atoms or alkoxy, $R_{12}$ is hydrogen or halogen or substituted or unsubstituted hydrocarbyl having from 1 to 20 carbon atoms, or inert functional group with the restriction that $R_{12}$ cannot be benzyl, and two or more of those groups can themselves be linked together to form further ring or rings with the exception that $R_7$ and $R_8$ cannot be linked to make a naphtyl group.

Preferably, $R_7$, $R_8$, $R_9$, $R_{10}$ and $R_{11}$ are hydrogen or alkyl or alkoxy, more preferably, $R_7$ and/or $R_{11}$ are hydrogen, methyl, isopropyl or tert-butyl, and/or $R_9$ is methyl, chlorine or methoxy. Most preferably, $R_7$, $R_8$, $R_{10}$ and $R_{11}$, are hydrogen and $R_9$ is methoxy or $R_7$ and $R_{11}$ are isopropyl and $R_8$, $R_9$ and $R_{10}$ are hydrogen.

$R_{12}$ is unsubstituted or substituted alkyl groups, unsubstituted or substituted aryl groups, or unsubstituted or substituted cycloalkyl groups, all these groups having at most 20 carbon atoms, preferably at most 10 carbon atoms, more preferably at most 6 carbon atoms. More preferably, $R_{12}$ is cyclohexyl.

Ligands of formula I and II result respectively from reacting 8-hydroquinoline-2-carbonyl of formula

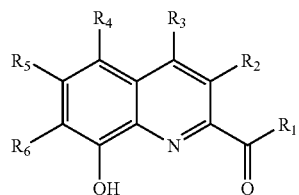

with an aromatic amine of formula

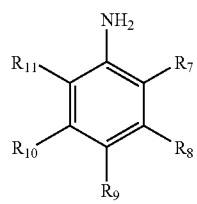

for ligand I
or with an aliphatic amine of formula

for ligand II

The present invention also discloses catalyst components of formula III and IV

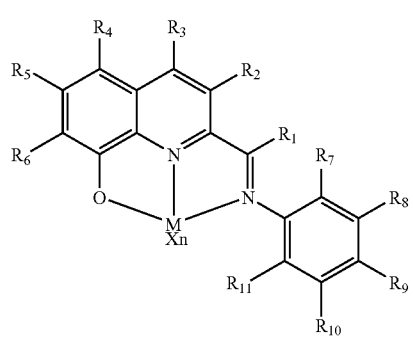

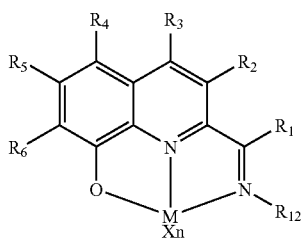

resulting respectively from the complexation of ligands I and II with metallic salt $MX_{n+1}$ in a solvent, wherein $R_1$ to $R_{12}$ are as described hereabove, M is a metal Group 3 to 10 of the Periodic Table, each X can be the same or different and is selected from halogen, substituted or unsubstituted hydrocarbyl having from 1 to 20 carbon atoms, substituted or unsubstituted aryloxy or alkoxy, and n+1 is the valence of M.

Preferably M is Ti, Zr, Hf, V, Cr, Mn, Fe, Co, Ni, Pd or rare earths. More preferably, it is Ti, Cr or Fe.

Preferably X is halogen, more preferably it is chlorine.

The solvent may be selected from dichloromethane or tetrahydrofuran and the complexation reaction is carried out at room temperature or at reflux.

The present invention further discloses an active catalyst system comprising the single site catalyst component of formula III or IV and an activating agent having an ionising action.

Suitable activating agents are well known in the art. The activating agent can be an aluminium alkyl represented by formula $AlR^+_n X_{3-n}$ wherein $R^+$ is an alkyl having from 1 to 20 carbon atoms and X is a halogen. The preferred alkylating agents are triisobutyl aluminium (TIBAL) or triethyl aluminium (TEAL).

Alternatively, it can be aluminoxane and comprise oligomeric linear and/or cyclic alkyl aluminoxanes represented by formula

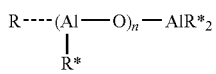

for oligomeric, linear aluminoxanes and by formula

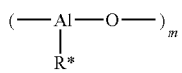

for oligomeric, cyclic aluminoxane,
wherein n is 1-40, preferably 10-20, m is 3-40, preferably 3-20 and R* is a $C_1$-$C_8$ alkyl group and preferably methyl.

The amount of activating is selected to give an Al/M ratio of from 100 to 3000, preferably of about 2000.

Suitable boron-containing activating agents may comprise a triphenylcarbenium boronate such as tetrakis-pentafluorophenyl-borato-triphenylcarbenium as described in EP-A-0427696, or those of the general formula [L'–H]+[B Ar$_1$ Ar$_2$ X$_3$ X$_4$]—as described in EP-A-0277004 (page 6, line 30 to page 7, line 7). The amount of boron-containing activating agent is selected to give B/M ratio of from 0.5 to 5, preferably of about 1.

In another embodiment, according to the present invention, the single site catalyst component of formula III or IV may be deposited on a conventional support. Preferably, the conventional support is silica impregnated with MAO. Alternatively and preferably, it can be an activating support such as fluorinated alumina silica.

The present invention further discloses a method for preparing an active catalyst system that comprises the steps of:

a) providing a ligand of formula I or II;
b) complexing the ligand of step a) with a metallic salt $MX_{n+1}$ in a solvent;
c) retrieving respectively the catalyst component III or IV;
d) activating with an activating agent having an ionising action;
e) optionally adding a cocatalyst;
f) retrieving an active oligomerisation or polymerisation catalyst system.

Alternatively, in step d), the catalyst component can be activated with an activating support.

The cocatalyst can be selected from triethylaluminium, triisobutylaluminum, tris-n-octylaluminium, tetraisobutyl-dialuminoxane or diethyl zinc.

This invention further discloses a method for the oligomerisation or polymerisation of ethylene and alpha-olefins that comprises the steps of:

a) injecting the active catalyst system into the reactor;
b) injecting the monomer and optional comonomer into the reactor;
c) maintaining under polymerisation conditions;
d) retrieving the oligomers or polymer.

The pressure in the reactor can vary from 0.5 to 50 bars, preferably from 5 to 25 bars.

The polymerisation temperature can range from 10 to 100° C., preferably from 50 to 85° C.

Preferably the monomer and optional comonomer are selected from ethylene, propylene or 1-hexene.

In another preferred embodiment according to the present invention, the optional comonomer is a polar functionalised alpha-olefin.

EXAMPLES

All reactions were performed using single-mode microwave reactor or standard Schlenk techniques or in an argon-filled glove-box. The starting materials and reagents, purchased from commercial suppliers, were used without purification. All solvents were dried and distilled before use over sodium and benzophenone for toluene, pentane and THF and over $CaH_2$ for methanol. $^1H$ and $^{13}C$ NMR spectra were recorded on a Bruker AC300 apparatus.

Preparation of Ligands.

Synthesis of 8-hydroxy-2-[N-(2,6-diisopropylphenylimino)methyl]-quinoline (L1)

173 mg (1 mmol) of 8-hydroxy-2-quinolinecarboxaldehyde and 177 mg (1 mmol) of 2,6-diisopropylaniline were dissolved in 2 mL of dry methanol in a microwave vial. One drop of glacial acetic acid was added and the vial was sealed. The yellow solution was warmed under microwave at a temperature of 120° C. for 20 minutes. The solution was cooled to room temperature (25° C.). After two days, yellow crystals appeared. They were filtered and washed with cold methanol and dried under vacuum. 228 mg of ligand L1 were obtained as yellow solid with a yield of 69%.

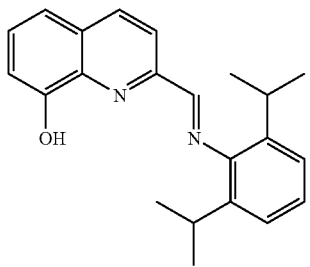

L1

NMR results were as follows.

$^1$H NMR (300 MHz, CDCl$_3$) δ (ppm): 1.22 (d, 12H, J=6.9 Hz, CH$_3$ iPr), 3.02 (sept, 2H, J=6.9 Hz, CH iPr), 7.23 (m, 4H, H7 and H benzyl), 7.43 (dd, 1H, J=8.3 Hz, H5), 7.56 (t, 1H, J=7.7 Hz, H6), 8.22 (s, 1H, OH), 8.31 (d, 1H, J=8.6 Hz, H3), 8.44 (d, 1H, J=8.6 Hz, H4), 8.48 (s, 1H, CH=N).

$^{13}$C{$^1$H} NMR (75 MHz, CDCl$_3$) δ (ppm): 23.4 (CH$_3$ iPr), 28.0 (CH iPr), 110.8 (C7), 117.9 (C5), 118.8 (C3), 123.1 (CH meta benzyl), 124.7 (CH para benzyl), 129.3 (C6), 129.3 (C4a), 136.9 (C4), 137.2 (C ortho benzyl), 137.7 (C—N), 148.3 (C2), 152.1 (C—OH), 152.5 (C8a), 162.6 (CH=N).

Synthesis of 8-hydroxy-2-[N-(2,6-dimethylphe-nylimino)methyl]-quinoline (L2)

The procedure was the same as that described for ligand L1 except that 121 mg (1 mmol) of 2,6-dimethylaniline were used as reagent. 261 mg of ligand L2 were obtained as yellow solid with a yield of 95%.

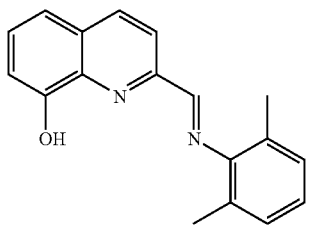

L2

NMR results were as follows.

$^1$H NMR (300 MHz, CDCl$_3$) δ (ppm): 2.22 (s, 6H, CH$_3$), 7.02 (t, 1H, J=7.5 Hz, H para benzyl), 7.13 (d, 2H, J=7.6 Hz, H meta benzyl), 7.25 (d, 1H, J=8 Hz, H7), 7.42 (d, 1H, J=8.2 Hz, H5), 7.55 (t, 1H, J=7.9 Hz, H6), 8.29 (d, 1H, J=8.6 Hz, H3), 8.45 (d, 1H, J=8.6 Hz, H4), 8.49 (s, 1H, CH=N).

$^{13}$C{$^1$H} NMR (75 MHz, CDCl$_3$) δ (ppm): 18.3 (CH$_3$), 110.7 (C7), 117.9 (C5), 118.8 (C3), 124.3 (CH para benzyl), 126.8 (C6), 128.2 (CH meta benzyl) 129.2 (C ortho benzyl), 129.3 (C4a), 136.8 (C4), 137.7 (C8a), 150.2 (C—N), 152.2 (C—OH), 152.6 (C2), 163.2 (CH=N).

Synthesis of 8-hydroxy-2-[N-(2,4,6-trimethylphe-nylimino)methyl]-quinoline (L3)

The procedure was the same as that described for ligand L1 except that 135 mg (1 mmol) of 2,4,6-trimethylaniline were used as reagent. 86 mg of ligand L3 were obtained as yellow crystals with a yield of 30%.

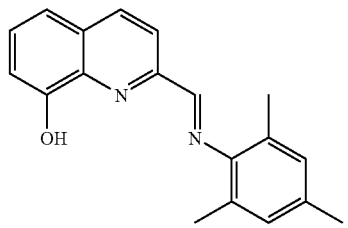

L3

NMR results were as follows.

$^1$H NMR (300 MHz, CDCl$_3$) δ (ppm): 2.20 (s, 6H, CH$_3$ ortho), 2.32 (s, 3H, CH$_3$ para), 6.95 (s, 2H, H meta benzyl), 7.25 (d, 1H, J=7.6 Hz, H7), 7.41 (d, 1H, J=8.2 Hz, H5), 7.54 (t, 1H, J=8 Hz, H6), 8.28 (d, 1H, J=8.6 Hz, H3), 8.44 (d, 1H, J=8.6 Hz, H4), 8.49 (s, 1H, CH=N).

$^{13}$C{$^1$H} NMR (75 MHz, CDCl$_3$) δ (ppm): 18.2 (CH$_3$ ortho), 20.7 (CH$_3$ para), 110.6 (C7), 117.9 (C5), 118.7 (C3), 126.8 (C ortho benzyl), 128.8 (CH meta benzyl), 129.1 (C6), 129.2 (C4a), 133.7 (C para benzyl), 136.7 (C4 et C8a), 147.7 (C—N), 152.3 (C—OH), 152.5 (C2), 162.9 (CH=N).

Synthesis of 8-hydroxy-2-[N-(2-tertbutylphe-nylimino)methyl]-quinoline (L4)

The procedure was the same as that described for ligand L1 except that 149 mg (1 mmol) of 2-tertbutylaniline were used as reagent. 224 mg of ligand L4 were obtained as yellow crystals with a yield of 74%.

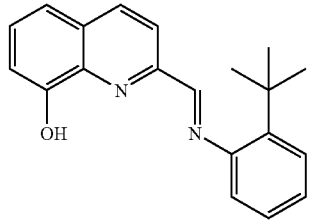

L4

NMR results were as follows.

$^1$H NMR (300 MHz, CDCl$_3$) δ (ppm): 1.52 (s, 9H, CH$_3$), 7.02 (m, 1H, H para benzyl), 7.26 (m, 3H, H benzyl), 7.42 (d, 1H, J=8.2 Hz, H7), 7.47 (d, 1H, J=7.6 Hz, H5), 7.54 (t, 1H, J=8 Hz, H6), 8.29 (d, 2H, J=8.6 Hz, H3 and OH), 8.38 (d, 1H, J=8.6 Hz, H4), 8.65 (s, 1H, CH=N).

$^{13}$C{$^1$H} NMR (75 MHz, CDCl$_3$) δ (ppm): 30.6 (CH$_3$), 35.7 (C(CH$_3$)$_3$), 110.8 (C7), 117.9 (C5), 119.1 (C3), 119.3 (CH benzyl), 126.3 (CH benzyl), 126.7 (C6), 127.1 (2 CH benzyl), 129.1 (C4a and CH benzyl), 136.9 (C4), 143.6 (C8a), 150.2 (C—N), 152.5 (C—OH), 152.8 (C2), 157.9 (CH=N).

Synthesis of 8-hydroxy-2-[N-(phenylimino)methyl]-quinoline (L5)

The procedure was the same as that described for ligand L1 except that 93 mg (1 mmol) of aniline were used as reagent. 160 mg of ligand L5 were obtained as orange solid with a yield of 65%.

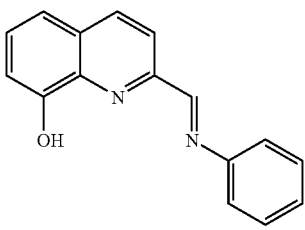

L5

Synthesis of 8-hydroxy-2-[N-(1-naphtylimino)methyl]-quinoline (L6)

The procedure was the same as that described for ligand L1 except that 143 mg (1 mmol) of 1-naphtylamine were used as reagent. 280 mg of ligand L6 were obtained as orange solid with a yield of 94%.

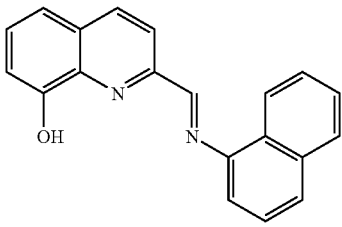

L6

NMR results were as follows.
$^1$H NMR (300 MHz, CDCl$_3$) δ (ppm): 7.25 (m, 2H, H7 and H naphtyl), 7.42 (d, 1H, J=8.3 Hz, H5), 7.53 (m, 4H, H6 and H naphtyl), 7.81 (d, 1H, J=8.3 Hz, H naphtyl), 7.90 (m, 1H, H naphtyl), 8.30 (d, 1H, J=8.5 Hz, H3), 8.43 (m, 1H, H naphtyl), 8.55 (d, 1H, J=8.6 Hz, H4), 8.86 (s, 1H, CH=N).
$^{13}$C{$^1$H} NMR (75 MHz, CDCl$_3$) δ (ppm): 110.7 (C7), 112.9 (CH naphtyl), 117.9 (C05), 119.4 (C3), 123.8 (CH naphtyl), 126.0 (2 CH naphtyl), 126.6 (CH naphtyl), 126.9 (CH naphtyl), 127.7 (CH naphtyl), 129.2 (C6 and C4a), 134.0 (C naphtyl), 136.7 (C4 and C naphtyl), 137.8 (C8a), 152.6 (C2, C—OH and C—N), 160.3 (CH=N).

Synthesis of 8-hydroxy-2-[N-(5,6,7,8-tetrahydronaphtylimino)methyl]-quinoline (L7)

The procedure was the same as that described for ligand L1 except that 152 mg (1 mmol) of 5,6,7,8-tetrahydronaphtylamine were used as reagent. 96 mg of ligand L7 were obtained as orange solid with a yield of 28%.

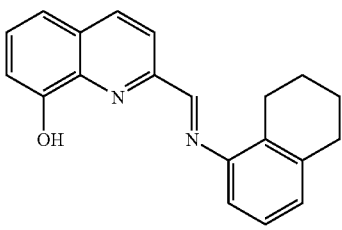

L7

NMR results were as follows.
$^1$H NMR (300 MHz, CDCl$_3$) δ (ppm): 1.86 (m, 4H, CH$_2$), 2.88 (m, 4H, CH$_2$), 6.57 (t, 1H, J=7.5 Hz, H3 naphtyl), 6.88 (d, 1H, J=7.5 Hz, H2 naphtyl), 7.04 (d, 1H, J=7.5 Hz, H4 naphtyl), 7.24 (d, 1H, J=7.6 Hz, H7), 7.39 (d, 1H, J=8.2 Hz, H5), 7.53 (t, 1H, J=7.9 Hz, H6), 8.16 (d, 1H, J=8.6 Hz, H3), 8.37 (d, 1H, J=8.6 Hz, H4), 8.65 (s, 1H, CH=N).

Synthesis of 8-hydroxy-2-[N-(4-methoxyphenylimino)methyl]-quinoline (L8)

The procedure was the same as that described for ligand L1 except that 123 mg (1 mmol) of 4-methoxyaniline were used as reagent. 275 mg of ligand L8 were obtained as orange solid with a yield of 99%.

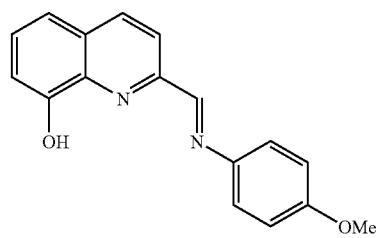

L8

NMR results were as follows.
$^1$H NMR (300 MHz, CDCl$_3$) δ (ppm): 3.87 (s, 3H, CH$_3$), 7.00 (d, 2H, J=9 Hz, H ortho benzyl), 7.23 (d, 1H, J=7.6 Hz, H7), 7.39 (m, 3H, H5 and H meta benzyl), 7.51 (t, 1H, J=8 Hz, H6), 8.22 (d, 1H, J=8.6 Hz, H3), 8.36 (d, 1H, J=8.6 Hz, H4), 8.78 (s, 1H, CH=N).
$^{13}$C{$^1$H} NMR (75 MHz, CDCl$_3$) δ (ppm): 55.5 (CH$_3$), 110.5 (C7), 114.5 (C5), 117.9 (2 CH meta benzyl), 119.2 (C3), 122.8 (2 CH ortho), 128.9 (C6), 136.5 (C4 and C4a), 137.8 (C8a), 143.4 (C—N), 152.8 (C—OH), 157.7 (C2 and CH=N), 159.2 (C-OMe).

Synthesis of 8-hydroxy-2-[N-(4-chlorophenylimino)methyl]-quinoline (L9)

173 mg (1 mmol) of 8-hydroxy-2-quinolinecarboxaldehyde and 128 mg (1 mmol) of 4-chloroaniline were dissolved in 2 mL of dry methanol. One drop of glacial acetic acid was added and the solution was stirred at room temperature overnight. The yellow solid that appeared was filtered, washed with cold methanol and dried under vacuum. 226 mg of ligand L9 were obtained as pale yellow solid with a yield of 80%.

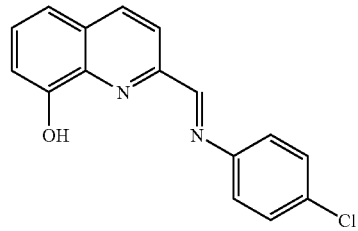

L9

NMR results were as follows,
$^1$H NMR (300 MHz, CDCl$_3$) δ (ppm): 7.24 (d, 1H, J=7.6 Hz, H7), 7.29 (d, 2H, J=8.7 Hz, H benzyl), 7.41 (m, 3H, H5 and H benzyl), 7.54 (t, 1H, J=8 Hz, H6), 8.19 (s, 1H, OH), 8.25 (d, 1H, J=8.6 Hz, H3), 8.36 (d, 1H, J=8.6 Hz, H4), 8.72 (s, 1H, CH=N).

$^{13}$C{$^1$H} NMR (75 MHz, CDCl$_3$) δ (ppm): 110.7 (C7), 117.9 (C5), 119.1 (C3), 122.5 (2 CH benzyl), 129.3 (C4a), 129.4 (C6 and 2 CH benzyl), 132.7 (C—Cl), 136.7 (C4 and C8a), 149.2 (C—N), 152.2 (C—OH), 152.5 (C2), 160.5 (CH═N).

Synthesis of 8-hydroxy-2-[N-(cyclohexylimino)methyl]-quinoline (L10)

173 mg (1 mmol) of 8-hydroxy-2-quinolinecarboxaldehyde and 99 mg (1 mmol) of cyclohexylamine were dissolved in 2 mL of dry methanol. One drop of glacial acetic acid was added and the solution stirred at room temperature overnight. The solvent was evaporated under vacuum to afford 254 mg of ligand L10 as orange solid with a quantitative yield.

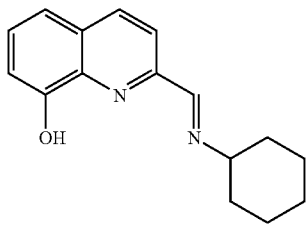

L10

NMR results were as follows.
$^1$H NMR (300 MHz, CDCl$_3$) δ (ppm): 1.41 (m, 4H, CH$_2$ cyclohexyl), 1.63-1.85 (m, 6H, CH$_2$ cyclohexyl), 3.37 (m, 1H, CH cyclohexyl), 4.26 (br s, 1H, OH), 7.19 (d, 1H, J=7.5 Hz, H7), 7.34 (d, 1H, J=8.2 Hz, H5), 7.48 (t, 1H, J=7.8 Hz, H6), 8.17 (s, 2H, H3 and H4), 8.54 (s, 1H, CH═N).
$^{13}$C{$^1$H} NMR (75 MHz, CDCl$_3$) δ (ppm): 24.7 (CH$_2$ meta cyclohexyl), 25.6 (CH$_2$ para cyclohexyl), 34.2 (CH$_2$ ortho cyclohexyl), 69.7 (CH—N), 110.3 (C7), 117.8 (C5), 119.1 (C3), 128.5 (C6), 128.9 (C4a), 136.4 (C4), 137.6 (C8a), 152.4 (C2), 152.9 (C—OH), 159.4 (CH═N).

Synthesis of 8-hydroxy-2-[N-(2,4,6-trifluorophenylimino)methyl]-quinoline (L11)

708 mg (4 mmol) of 8-hydroxy-2-quinolinecarboxaldehyde and 606 mg (4 mmol) of 2,4,6-trifluoroaniline were dissolved in 4 mL of dry methanol in a microwave vial. Four drops of glacial acetic acid were added and the vial was sealed. The yellow solution was warmed under microwave at a temperature of 120° C. for 20 minutes. The solution was cooled to room temperature (25° C.). The solvent was evaporated under vacuum to afford a yellow oil purified by column chromatography (SiO$_2$, heptane:diethyl ether 7:3). 264 mg of ligand L11 were obtained as yellow solid with a yield of 22%.

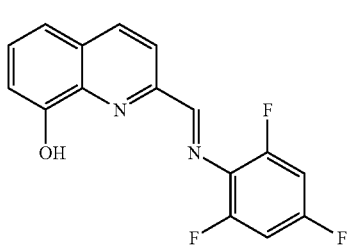

L11

NMR results were as follows.
$^1$H NMR (300 MHz, CDCl$_3$) δ (ppm): 6.83 (m, 2H, H trifluorophenyl), 7.26 (t, 1H, J=7.7 Hz, H7), 7.40 (d, 1H, J=8.2 Hz, H5), 7.56 (t, 1H, J=8.2 Hz, H6); 8.19 (br s, 1H, OH), 8.27 (d, 1H, J=8.6 Hz, H3), 8.40 (d, 1H, J=8.6 Hz, H4), 8.93 (s, 1H, CH═N).

Synthesis of 8-hydroxy-2-[N-(pentafluorophenylimino)methyl]-quinoline (L12)

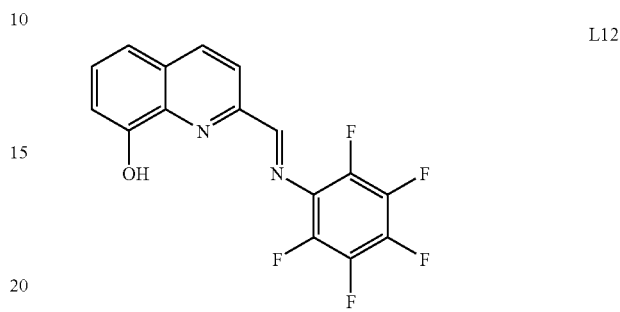

L12

708 mg (4 mmol) of 8-hydroxy-2-quinolinecarboxaldehyde and 740 mg (4 mmol) of pentafluoroaniline were dissolved in 4 mL of dry methanol in a microwave vial. Four drops of glacial acetic acid were added and the vial was sealed. The yellow solution was warmed under microwave at a temperature of 120° C. for 20 minutes. The solution was cooled to room temperature (25° C.). After one night at 40° C., yellow crystals appeared. They were filtered and washed with cold methanol and dried under vacuum. 740 mg of ligand L12 were obtained as pale yellow solid with a yield of 55%.

NMR results were as follows.
$^1$H NMR (300 MHz, CDCl$_3$) δ (ppm): 7.26 (d, 1H, J=7.3 Hz, H7), 7.42 (d, 1H, J=8.1 Hz, H5), 7.59 (t, 1H, J=8.1 Hz, H6), 8.14 (br s, 1H, OH), 8.30 (d, 1H, J=8.6 Hz, H3), 8.39 (d, 1H, J=8.6 Hz, H4), 8.90 (s, 1H, CH═N).
$^{13}$C{$^1$H} NMR (75 MHz, CDCl$_3$) δ (ppm): 111.0 (C7), 118.03 (C5), 119.0 (C3), 125.5 (CN), 129.6 (C4a), 130.1 (C6), 136.3 (C meta fluorophenyl), 137.0 (C4 and C8a), 137.9 (C—N), 140.0 (C ortho fluorophenyl), 141.8 (C para fluorophenyl), 151.3 (C—OH), 152.7 (C2), 168.5 (CH═N).

Synthesis of 8-hydroxy-2-[N-(3,5-(trifluoromethyl)phenylimino)methyl]-quinoline (L13)

The procedure was the same as that described for ligand L10 except that 458 mg (2 mmol) of 3,5-trifluoromethylaniline were used as reagent 631 mg of ligand L13 were obtained as yellow solid with a yield of 82%.

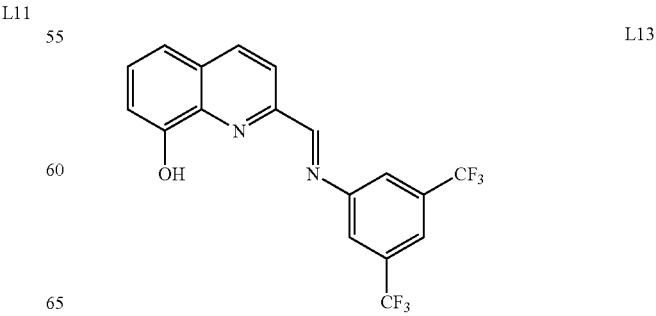

L13

Synthesis of 8-hydroxy-2-[N-(2,6-dichlorophenylimino)methyl]-quinoline (L14)

The procedure was the same as that described for ligand L11 except that 330 mg (2 mmol) of 2,6-dichloroaniline were used as reagent. Purification by column chromatography used heptane:ethyl acetate in 8:2 proportion. 150 mg of ligand L14 were obtained as pale yellow solid with a yield of 24%.

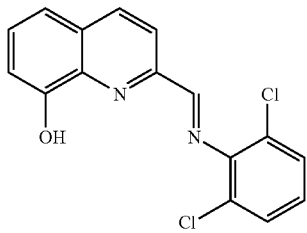

L14

NMR results were as follows.

$^1$H NMR (300 MHz, CDCl$_3$) δ (ppm): 7.08 (t, 1H, J=8.2 Hz, H7), 7.26 (d, 1H, J=7.6 Hz, H5), 7.42 (m, 3H, H dichlorophenyl), 7.57 (t, 1H, J=7.8 Hz, H6), 8.18 (br s, 1H, OH), 8.32 (d, 1H, J=8.6 Hz, H3), 8.46 (d, 1H, J=8.6 Hz, H4), 8.64 (s, 1H, CH=N).

Preparation of Complexes.

Synthesis of Ti(IV) Complexes A.

332 mg (1 mmol) of ligand L1 were dissolved in 5 mL of THF and cooled to a temperature of −78° C. 1 mmol of n-butyl lithium (C=1,6M in hexane) was added dropwise. The orange solution was stirred for 2 hours at room temperature. 1 mL (1 mmol) of TiCl$_4$ (C=1M in toluene) was dissolved in 5 mL of THF and cooled to a temperature of −78° C. The solution of anionic ligand was added dropwise to the solution of TiCl$_4$, and it was stirred at room temperature overnight. The mixture was evaporated to dryness and the complex was extracted with 10 mL of dry dichloromethane. The filtrate was evaporated and the residue was washed with 3 mL of diethyl ether and twice with 10 mL of pentane. The resulting solid was dried under vacuum to afford 482 mg of complex A1 as dark red powder with a yield of 96%.

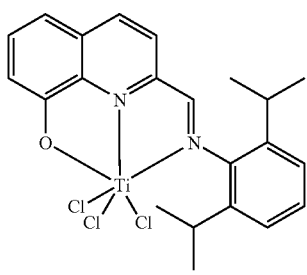

A1

Complexes A2, A3, A4 and A8 to A14 were obtained from ligands L2, L3, L4 and L8 to L14 following the same procedure as that used for obtaining complex A1 from ligand L1.

The yields are summarized in Table 1.

TABLE I

| Ligand | Complex | Color of complex | Yield (%) |
|---|---|---|---|
| L1 | A1 | dark red | 96 |
| L2 | A2 | brown | 88 |
| L3 | A3 | dark orange | 99 |
| L4 | A4 | red orange | 96 |
| L8 | A8 | dark red | 96 |
| L9 | A9 | dark red | 99 |
| L10 | A10 | dark red | 87 |
| L11 | A11 | dark red | 65 |
| L12 | A12 | dark orange | 56 |
| L13 | A13 | dark orange | 68 |
| L14 | A14 | dark red | 69 |

Synthesis of Zr(IV) Complexes B1.

166 mg (0.5 mmol) of ligand L1 was dissolved in 5 mL of THF and cooled to a temperature of −78° C. 0.5 mmol of n-butyl lithium (C=1.6 M in hexane) was added drop-wise. The dark red solution was stirred for 30 minutes at room temperature. 0.5 mmol of ZrCl$_4$ was dissolved in 5 mL of THF and cooled to a temperature of −78° C. The solution of the anionic ligand was added drop-wise to the solution of ZrCl$_4$. The resulting solution was stirred overnight under reflux at a temperature of 70° C. The mixture was evaporated to dryness and the complex was extracted with 10 mL of dry dichloromethane. The filtrate was evaporated and the residue was washed with 3 mL of diethyl ether and twice with 10 mL of pentane. The resulting solid was dried under vacuum to afford 221 mg of complex B1 as red powder with a yield of 84%.

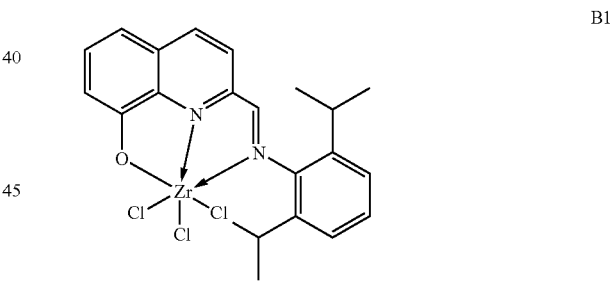

B1

Synthesis of V(III) Complexes C1.

193 mg (0.5 mmol) of ligand L1 was dissolved in 5 mL of THF and cooled to a temperature of −78° C. 0.5 mmol of n-butyl lithium (1.6 M in hexane) was added drop-wise. The solution was stirred for 30 minutes at room temperature. 0.5 mmol of (THF)$_3$VCl$_3$ was dissolved in 5 mL of THF and cooled to a temperature of −78° C. The solution of the anionic ligand was added drop-wise to the solution of VCl$_3$. The resulting solution was stirred overnight at room temperature. The mixture was evaporated to dryness and the complex was extracted with 10 mL of dry dichloromethane. The filtrate was concentrated to approximately 2 mL, and 10 mL of pentane were added. Solvents were filtered off and the solid was washed twice with pentane. The resulting solid was dried under vacuum to afford 179 mg of complex C1 as yellow brown powder with a yield of 79%.

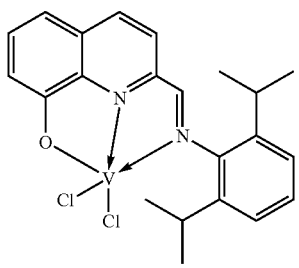

C1

Synthesis of Cr(III) Complexes D.

100 mg (0.3 mmol) of ligand L1 were dissolved in 5 mL of THF and cooled to a temperature of −15° C. One equivalent of n-butyl lithium (C=1.6M in hexane) was added dropwise. The solution was stirred for 30 minutes and added to a solution of 112 mg (0.3 mmol) of $(THF)_3CrCl_3$ dissolved in 5 mL of THF. The solution was stirred at room temperature overnight. The mixture was concentrated to approximately 2 mL and 10 mL of pentane were then added. Solvents were filtered off and the solid was washed twice with pentane. The resulting solid was dried under vacuum to afford 131 mg of complex D1 as brown powder with a yield of 95%.

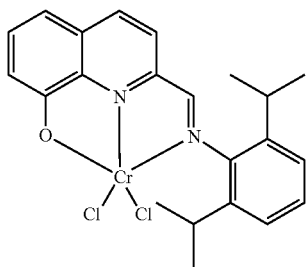

D1

Complexes D2, D3, D4, D6, D8 to D14 were obtained from ligands L2 μL3, L4, L6, L8 to L14 following the same procedure as that used for obtaining complex D1 from ligand L1.

The yields are summarized in Table II.

TABLE II

| Ligand | Complex | Color of complex | Yield (%) |
|---|---|---|---|
| L1 | D1 | brown | 95 |
| L2 | D2 | brown | 90 |
| L3 | D3 | brown | 92 |
| L4 | D4 | dark yellow | 99 |
| L6 | D6 | brown | 99 |
| L8 | D8 | brown | 91 |
| L9 | D9 | brown | 98 |
| L10 | D10 | dark red | 93 |
| L11 | D11 | dark red | 99 |
| L12 | D12 | dark red | 83 |
| L13 | D13 | brown | 97 |
| L14 | D14 | brown | 91 |

Synthesis of Fe(III) Complexes E.

166 mg (0.5 mmol) of ligand L1 were dissolved in 5 mL of THF and cooled to a temperature of −15° C. 0.5 mmol of n-butyl lithium (C=1,6M in hexane) were added dropwise. The solution was stirred for 30 minutes and added to a solution of 80 mg (0.5 mmol) of anhydrous $FeCl_3$ dissolved in 5 mL of THF. The solution was stirred at room temperature overnight. The mixture was concentrated to approximately 2 mL and then 10 mL of pentane were added. Solvents were filtered off and the solid was washed twice with pentane. The resulting solid was dried under vacuum to afford complex E1 as dark green powder.

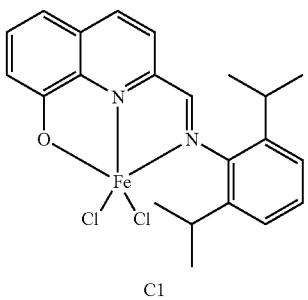

E1

Complexes E2, E3, E4, E6, E8, E9 and E10 were obtained from ligands L2, L3, L4, L6, L8, L9 and L10 following the same procedure as that used for obtaining complex E1 from ligand L1.

The yields are summarized in Table III.

TABLE III

| Ligand | Complex | Color of complex | Yield (%) |
|---|---|---|---|
| L1 | E1 | yellow | 37 |
| L2 | E2 | dark brown | 65 |
| L3 | E3 | dark green | 50 |
| L4 | E4 | dark green | 61 |
| L6 | E6 | dark green | 99 |
| L8 | E8 | dark brown | 85 |
| L9 | E9 | dark green | 99 |
| L10 | E10 | dark yellow | 99 |

Polymerisation of Ethylene.

Ethylene polymerisation reactions were performed in a 20 mL stainless steel autoclave containing a glass insert, fitted with mechanical stirring, external thermocouple and pressure gauge and controlled by a computer. In a typical reaction run, the temperature was set at 50° C. or 80° C. and 4 mL of dry solvent (toluene or n-heptane) were introduced into the reactor. In a argon-filled glove box, about 4 mg (5 μmol) of the appropriate catalyst were weighted, activated with methylaluminoxane (MAO) (30% wt in toluene) in an appropriate amount to obtain a ratio [Al]:[M] of 2000, and then diluted with toluene to obtain a final volume of 2 mL. 200 μL of the solution of activated catalyst were placed inside the reactor. The injection loop was rinsed with 800 μL of solvent. The ethylene pressure was raised to 15 bar and it was continuously fed into the reactor. After either 1 hour or an ethylene consumption of 12 mmol, the reactor was cooled down and depressurized, then the reaction was quenched with isopropanol and the solution analysed by gas chromatography. The gas chromatographic (GC) analysis of the reaction products was performed on a Trace GC apparatus with a Petrocol capillary column (methyl silicone, 100 m long, i.d. 0.25 mm and film thickness of 0.5 μm) working at a temperature of 35° C. for 15 min and then heating at a rate of 5° per minute up to a temperature of 250° C. The polymerisation conditions and results are displayed in Tables IV to VIII.

TABLE IV

| Run | Complex | T (° C.) | solvent | m PE (mg) | Activity (kg/mol/h) |
|---|---|---|---|---|---|
| 1 | A1 | 80 | toluene | 154 | 304 |
| 2 | A1 | 80 | n-heptane | 570 | 1128 |
| 3 | A1 | 50 | toluene | 125 | 247 |
| 4 | A1 | 50 | n-heptane | 213 | 420 |

TABLE V

| | DSC | |
|---|---|---|
| Run | Tm (° C.) | ΔH (J·g$^{-1}$) |
| 1 | 132.4 | 143.0 |
| 2 | 135.1 | 159.3 |
| 3 | 134.3 | 147.3 |
| 4 | 133.6 | 118.1 |

All reactions were performed with 0.5 μmol of the Ti-based catalyst dissolved in 5 mL of solvent, at polymerisation temperatures of 50° C. or 80° C. as indicated in Table III, under an ethylene pressure of 15 bars, with MAO as activating agent in an amount suitable to give a [Al]:[Ti] molar ratio of 2000. Polymerisations were stopped after 1 hour.

Activities are expressed in kg of polyethylene per mol Ti per hour.

The obtained polymers were insoluble in hot trichlorobenzene and could not be characterised by GPC.

TABLE VI

| Run | Complex. | m PE (mg) | Activity (kg/mol/h) | % C4 Total | % α-C4 | % C6 Total | % α-C6 | % > C6 | Tm (° C.) |
|---|---|---|---|---|---|---|---|---|---|
| 5 | D1 | 9 | 106 | 24 | 99 | 28 | 84 | 47 | 134.1 |
| 6 | D2 | 9 | 61 | 26 | 96 | 26 | 84 | 48 | / |
| 7 | D3 | 8 | 79 | 28 | 97 | 27 | 76 | 45 | / |
| 8 | D4 | 7 | 47 | 42 | 93 | 24 | 59 | 34 | 135.4 |
| 9 | D6 | 11 | 90 | 32 | 97 | 27 | 82 | 41 | 134.1 |
| 10 | D8 | 13 | 273 | 70 | 98 | 20 | 74 | 10 | 129.4 |
| 11 | D9 | 8 | 39 | C4, C6, C8 oligomers traces | | | | | / |
| 12 | D14 | 11 | 62 | C4, C6, C8 oligomers traces | | | | | 132.8 |
| 13 | D1 | 15 | 37 | C4, C6 oligomers traces | | | | | 135.6 |
| 14 | D2 | 11 | 42 | 24 | 97 | 33 | 69 | 43 | 131.1 |
| 15 | D3 | 11 | 40 | 17 | 97 | 38 | 39 | 45 | 131.6 |
| 16 | D4 | 14 | 30 | C4, C6 oligomers traces | | | | | 134.0 |
| 17 | D6 | 17 | 48 | C4 to C14 oligomers traces | | | | | 133.7 |
| 18 | D8 | 18 | 100 | 61 | 98 | 25 | 56 | 14 | 130.9 |
| 19 | D9 | 14 | 53 | C4, C6, C8 oligomers traces | | | | | / |
| 20 | D14 | 20 | 43 | C4, C6, C8 oligomers traces | | | | | 132.2 |

All reactions were performed with 0.5 μmol of the Cr-based catalyst dissolved in 5 mL of solvent, at a polymerisation temperature of 50° C., under a pressure of ethylene of 15 bars, with MAO as activating agent in an amount suitable to give a [Al]:[Cr] molar ratio of 2000. Polymerisations were stopped after a period of time of 1 hour. Runs 5 to 11 were performed in toluene, runs 12 to 20 were performed in n-heptane.

Activities are expressed in kg of ethylene consumed per mol Cr per hour.

The percentages of C4, C6 and >C6 were calculated by GC analysis as well as the percentages of α-C2n in C2n.

Most of the obtained PE were insoluble in hot trichlorobenzene and could not be characterised by GPC, with the exception of PE obtained from runs 12 and 20. Table VII displays the number average molecular weight Mn, the weight average molecular weight Mw and the polydispersity index D that is the ratio Mw/Mn.

TABLE VII

| | | GPC | | |
|---|---|---|---|---|
| Run | Complex | Mw | Mn | D |
| 12 | D14 | 446727 | 9561 | 46.7 |
| 20 | D14 | 369064 | 8949 | 41.2 |

Polymerisation of Ethylene with Supported Catalysts.

Ethylene polymerisation reactions were carried out in a 130 ml stainless steel autoclave equipped with mechanical stirring and a stainless steel injection cylinder. In a typical reaction run, the reactor was first dried under nitrogen flow at 100° C. during 10 min. Then it was cooled down to the reaction temperature (50° or 85° C.) and 35 ml of isobutane were introduced into the reactor with a syringe pump. The pressure was adjusted to the desired value (14.8 or 23.8 bar) with ethylene. In an argon-filled glove box, 0.1 ml of TiBAl (10% wt in hexane), the appropriate supported catalyst (2% wt on MAO impregnated silica) and 0.6 ml of n-hexane were placed into the injection cylinder. The valve was closed and the cylinder was connected to the reactor under nitrogen flow. The active catalyst mixture was then introduced into the reactor with 40 ml of isobutane. After 1 hour, the reactor was cool down to room temperature and slowly depressurised, and the polymer was recovered. The polymerisation results are displayed in Table VIII.

TABLE VIII

| Complex | Amount supported catalyst (mg) | mPE (g) | Productivity (g/g·h) |
|---|---|---|---|
| A1 | 123.4 | 1.0 | 8 |
| D8 | 303 | 1.2 | 4 |

All reactions were performed in isobutane, at a polymerisation temperature of 85° C., under a pressure of ethylene of 23.8 bars, with 25.6 mg of TiBAl as cocatalyst. Polymerisations were stopped after a period of time of 1 hour.

Copolymerisation of Ethylene with Propylene.

The procedure was the same as that described above with MAO except that the reaction was performed at 80° C., and that the reactor was first pressurised with propylene, followed by ethylene to a final pressure of 19 bar in order to obtain a mixture of 10% of propylene (molar fraction) in ethylene. The polymerisation results are displayed in Table IX.

TABLE IX

| Run | Complex | m Polymer (mg) | Activity (kg/mol/h) | DSC Tm (° C.) | ΔH (J·g$^{-1}$) | % Me branching |
|---|---|---|---|---|---|---|
| 21 | A1 | 280 | 523 | 126 | 130.0 | 1.8 |

The reaction was performed with 0.5 μmol of catalyst dissolved in 5 mL of n-heptane, at a temperature 80° C. under an ethylene pressure of 19 bars and with MAO as activating agent. The amount of activating agent MAO was adjusted to yield a ratio [Al]:[Ti] of 2000.

Activities are expressed in kg copolymer per mol of Ti per hour.

The obtained polymers were insoluble in hot trichlorobenzene and could not be characterised by GPC.

Polymerisation of Ethylene

Ethylene polymerisation reactions were performed in a 24 parallel reactors unit containing glass inserts of 50 ml and magnetical stirrers. In a typical reaction run, the catalyst was introduced into the glass insert. Then the activator (MAO or IBAO) and the solvent (22 to 24 ml of heptane) were added. The glass insert was sealed with a septum and placed into the 24 parallel reactors unit. While closing the reactor, the septum was pierced by a needle. The stirring was set at 1000 rpm and the temperature was set at 80° C. Then the pressure was raised to 22 bar of ethylene. These conditions were maintained during 20 min. The polymerisation results are displayed in Tables X to XIII.

TABLE X

| COMPLEX | M* (g/mol) | COMPLEX (mg) | COMPLEX (μmol) | Al/M | FLUFF (g) | PRODUCTIVITY (kg/g/h) | PRODUCTIVITY (kg/mmol·h) |
|---|---|---|---|---|---|---|---|
| C1 | 453.3 | 1.236 | 2.73 | 277 | 0.030 | 73 | 0.03 |
| C1 | 453.3 | 1.306 | 2.88 | 262 | 0.036 | 83 | 0.04 |
| D1 | 454.3 | 0.95 | 2.09 | 361 | 0.12 | 379 | 0.17 |
| D1 | 454.3 | 1.356 | 2.98 | 253 | 0.22 | 487 | 0.22 |

The polymerisation conditions were as follows: 22 mL heptane, 2.6 ml IBAO, 22 bar ethylene, 80° C., 20 min., 1000 rpm.
*M represents the molecular mass of the complex expressed in g/mol.

TABLE XI

| COMPLEX | M (g/mol) | COMPLEX (mg) | COMPLEX (μmol) | MAO (ml) | FLUFF (g) | PRODUCTIVITY (kg/g/h) | PRODUCTIVITY (kg/mmol·h) |
|---|---|---|---|---|---|---|---|
| B1 | 529.0 | 1.053 | 1.99 | 1.2 | 1.04 | 2963 | 1.58 |
| B1 | 529.0 | 1.013 | 1.91 | 1.2 | 0.96 | 2843 | 1.52 |
| C1 | 453.3 | 0.949 | 2.09 | 1.2 | 0.59 | 1865 | 0.85 |
| C1 | 453.3 | 1.243 | 2.74 | 1.2 | 0.57 | 1376 | 0.63 |
| A1 | 485.7 | 0.476 | 0.98 | 0.6 | 1.26 | 7950 | 3.90 |
| A1 | 485.7 | 0.476 | 0.98 | 0.6 | 1.21 | 7634 | 3.74 |

The polymerisation conditions were as follows: 23 mL heptane, Al/M~2000, 22 bar ethylene, 80° C., 20 min., 1000 rpm.

TABLE XII

| COMPLEX | M (g/mol) | COMPLEX (mg) | COMPLEX (μmol) | Al/M | FLUFF (g) | PRODUCTIVITY (kg/g/h) | PRODUCTIVITY (kg/mmol·h) |
|---|---|---|---|---|---|---|---|
| D11 | 424.14 | 0.936 | 2.21 | 342 | 0.143 | 458 | 0.20 |
| D11 | 424.14 | 1.066 | 2.51 | 301 | 0.13 | 366 | 0.16 |
| D12 | 460.1 | 0.956 | 2.08 | 364 | 0.11 | 345 | 0.16 |
| D12 | 460.1 | 0.96 | 2.09 | 362 | 0.09 | 281 | 0.13 |
| D14 | 439.1 | 0.975 | 2.22 | 340 | 0.06 | 185 | 0.08 |
| D14 | 439.1 | 1.3 | 2.96 | 255 | 0.062 | 143 | 0.06 |
| D13 | 506.17 | 1.07 | 2.11 | 357 | 0.15 | 421 | 0.22 |
| D13 | 506.17 | 1.035 | 2.04 | 369 | 0.16 | 464 | 0.24 |
| D9 | 404.6 | 1.294 | 3.20 | 236 | 0.12 | 278 | 0.11 |
| D9 | 404.6 | 1.099 | 2.72 | 278 | 0.16 | 437 | 0.18 |
| D1 | 454.3 | 0.95 | 2.09 | 361 | 0.12 | 379 | 0.17 |
| D1 | 454.3 | 1.356 | 2.98 | 253 | 0.22 | 487 | 0.22 |

The polymerisation conditions were as follows: 22 ml heptane, 2.6 ml IBAO, 22 bar ethylene, 80° C., 20 min., 1000 rpm.

TABLE XIII

| COMPLEX | M (g/mol) | COMPLEX (mg) | COMPLEX (μmol) | FLUFF (g) | PRODUCTIVITY (g/g/h) | PRODUCTIVITY (kg/mmol·h) | DSC Tm (° C.) | DSC ΔH (J·g$^{-1}$) |
|---|---|---|---|---|---|---|---|---|
| A13 | 537.5 | 0.543 | 1.01 | 0.54 | 2983 | 1.62 | 133.2 | 28.9 |
| A13 | 537.5 | 0.543 | 1.01 | 0.56 | 3094 | 1.68 | 131.6 | 21.9 |
| A11 | 455.5 | 0.487 | 1.07 | 0.96 | 5914 | 2.72 | 137.0 | 117.3 |
| A11 | 455.5 | 0.487 | 1.07 | 1.12 | 6899 | 3.17 | 137.2 | 129.8 |
| A12 | 491.4 | 0.487 | 0.99 | 1.27 | 7823 | 3.88 | 136.8 | 141.6 |
| A12 | 491.4 | 0.487 | 0.99 | 1.13 | 6961 | 3.46 | 137.5 | 126.9 |
| A14 | 470.4 | 0.508 | 1.08 | 1.14 | 6732 | 3.20 | 136.1 | 132.8 |
| A14 | 470.4 | 0.508 | 1.08 | 1.18 | 6969 | 3.31 | 137.7 | 143.5 |
| A9 | 435.94 | 0.588 | 1.35 | 1.14 | 5821 | 2.56 | 136.9 | 125.6 |

TABLE XIII-continued

| COMPLEX | M (g/mol) | COMPLEX (mg) | (μmol) | FLUFF (g) | PRODUCTIVITY (g/g/h) | (kg/mmol · h) | DSC Tm (° C.) | ΔH (J · g$^{-1}$) |
|---|---|---|---|---|---|---|---|---|
| A9 | 435.94 | 0.588 | 1.35 | 1.18 | 6026 | 2.65 | 136.4 | 124.6 |
| A1 | 485.7 | 0.476 | 0.98 | 1.26 | 7950 | 3.90 | 135.8 | 133.8 |
| A1 | 485.7 | 0.476 | 0.98 | 1.21 | 7634 | 3.74 | 134.4 | 116.3 |

The polymerisation conditions were as follows: 24 ml heptane, 0.6 ml MAO, Al/M~2000, 22 bar ethylene, 80° C., 20 min., 1000 rpm.

The invention claimed is:

1. A catalyst component of formula III

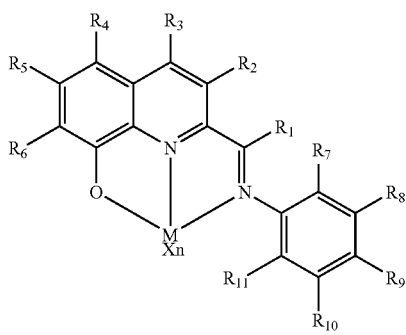

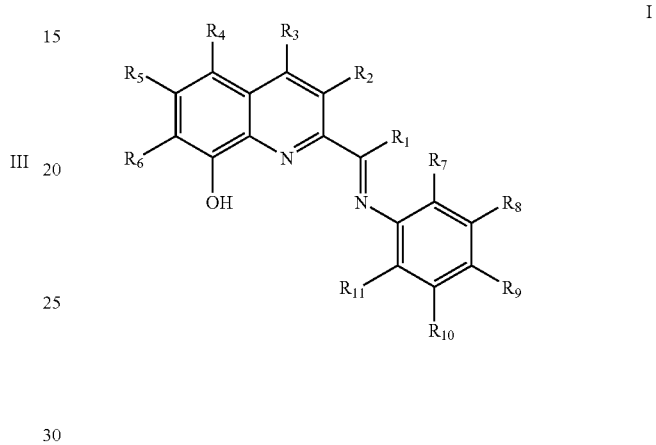

wherein M is a metal of Group 3 to 10 of the Periodic Table, wherein each X can be the same or different and is selected from halogen, substituted or unsubstituted hydrocarbyl having from 1 to 20 carbon atoms, or substituted or unsubstituted aryloxy or alkoxy, wherein n+1 is the valence of M, wherein $R_1$, $R_2$, $R_3$; $R_4$, $R_5$, $R_6$, $R_7$, $R_8$, $R_9$, $R_{10}$, and $R_{11}$ are each independently selected from hydrogen, halogen, or unsubstituted or substituted hydrocarbyl having from 1 to 20 carbon atoms, wherein two or more of $R_1$, $R_2$, $R_3$, $R_4$, $R_5$, $R_6$, $R_7$, $R_8$, $R_9$, $R_{10}$, and $R_{11}$ can themselves be linked together to form further ring or rings.

2. The catalyst component of claim 1 wherein M is Ti, Cr or Fe.

3. The catalyst component of claim 1 wherein $R_7$ and $R_{11}$ are selected from the group consisting of are hydrogen, methyl, isopropyl or tert-butyl.

4. The catalyst component of claim 3, wherein $R_9$ is methoxy.

5. The catalyst component of claim 1 wherein $R_7$, $R_8$, $R_{10}$ and $R_{11}$ are hydrogen and $R_9$ is methoxy.

6. The catalyst component of claim 1 wherein $R_7$ and $R_{11}$ are isopropyl and $R_8$, $R_9$ and $R_{10}$ are hydrogen.

7. The catalyst component of claim 1 wherein said catalyst component is prepared by complexation reaction of metallic salt $MX_{n+1}$ in a solvent with a ligand of formula I wherein M, X, n, $R_1$, $R_2$, $R_3$, $R_4$, $R_5$, $R_6$, $R_7$, $R_8$, $R_9$, $R_{10}$, and $R_{11}$ are as defined in claim 1.

8. An active catalyst system comprising the catalyst component of claim 7, an activating agent selected from an aluminium- or boron- containing complex and optionally a cocatalyst.

9. The active catalyst system of claim 8 wherein the cocatalyst is triethylaluminium, triisobutylaluminum, tris-n-octylaluminum, tetraisobutyldialuminoxane or diethyl zinc.

10. A method for preparing the active catalyst system of claim 8 that comprises the steps of:
 a) providing a ligand of formula I;
 b) complexing the ligand of step a) with a metallic salt $MX_{n+}$ in a solvent;
 c) retrieving the catalyst component of formula III;
 d) activating with an activating agent having an ionising action;
 e) optionally adding a cocatalyst;
 f) retrieving an active catalyst system.

11. A method for the oligomerisation or polymerisation of ethylene and alpha-olefins that comprises the steps of:
 a) injecting the active catalyst system of claim 8 into a reactor;
 b) injecting the monomer and optional comonomer into the reactor;
 c) maintaining the reactor under polymerisation conditions;
 d) retrieving oligomers or polymer.

12. The method of claim 11 wherein the monomer is ethylene or propylene.

13. An active catalyst system comprising the catalyst component of claim 1, an activating support and optionally a cocatalyst.

14. The active catalyst system of claim 13 wherein the activating support is silica impregnated with aluminoxane.

* * * * *

UNITED STATES PATENT AND TRADEMARK OFFICE
CERTIFICATE OF CORRECTION

PATENT NO.       : 7,932,331 B2                    Page 1 of 1
APPLICATION NO.  : 12/282261
DATED            : April 26, 2011
INVENTOR(S)      : Caroline Hillairet et al.

It is certified that error appears in the above-identified patent and that said Letters Patent is hereby corrected as shown below:

Claim 3, Column 19, Line 56, the word --are-- should be removed after the word "of".
    Claim 9, Column 20, Line 38, the word --triethylaluminium-- should be "triethylaluminum".

Signed and Sealed this
Ninth Day of August, 2011

David J. Kappos
*Director of the United States Patent and Trademark Office*